United States Patent [19]
Sun et al.

[11] Patent Number: 5,993,787
[45] Date of Patent: Nov. 30, 1999

[54] COMPOSITION BASE FOR TOPICAL THERAPEUTIC AND COSMETIC PREPARATIONS

[75] Inventors: Ying Sun, Somerville; Jue-Chen Liu, Belle Mead; Elisabeth S. Kimbleton, Princeton; Jonas C. T. Wang, Robbinsville, all of N.J.

[73] Assignee: Johnson & Johnson Consumer Products, Inc., Skillman, N.J.

[21] Appl. No.: 08/713,691

[22] Filed: Sep. 13, 1996

[51] Int. Cl.$^6$ ..................................................... A61K 7/42
[52] U.S. Cl. .......................... 424/59; 424/401; 424/63; 424/65; 424/70.1; 514/817; 514/844; 514/852; 514/858; 514/859; 514/880; 514/944
[58] Field of Search .................................. 424/59, 63, 65, 424/70.1, DIG. 4, 401; 514/817, 844, 852, 858, 859, 880, 944

[56] References Cited

U.S. PATENT DOCUMENTS

| | | | |
|---|---|---|---|
| 3,899,578 | 8/1975 | Bird et al. | 424/81 |
| 4,017,615 | 4/1977 | Shastri et al. | 424/241 |
| 4,244,948 | 1/1981 | Boghosian et al. | 424/230 |
| 4,393,076 | 7/1983 | Noda et al. | 424/317 |
| 4,469,627 | 9/1984 | Trombone | 252/548 |
| 4,542,020 | 9/1985 | Jackson et al. | 514/31 |
| 4,713,243 | 12/1987 | Schiraldi et al. | 424/151 |
| 4,820,724 | 4/1989 | Nimni | 514/396 |
| 4,820,784 | 4/1989 | Nimni | 514/396 |
| 4,867,970 | 9/1989 | Newsham et al. | 424/81 |
| 4,869,899 | 9/1989 | Burghart et al. | 424/78 |
| 4,883,792 | 11/1989 | Timmins et al. | 514/169 |
| 4,963,591 | 10/1990 | Fourman et al. | 514/944 |
| 5,002,938 | 3/1991 | Wang et al. | 514/171 |
| 5,110,809 | 5/1992 | Wang et al. | 514/171 |
| 5,174,995 | 12/1992 | Davis | 424/400 |
| 5,219,877 | 6/1993 | Shah et al. | 514/399 |
| 5,292,532 | 3/1994 | Bombart | 424/405 |
| 5,310,545 | 5/1994 | Eisen | 424/49 |
| 5,358,959 | 10/1994 | Halperin et al. | 514/396 |
| 5,446,070 | 8/1995 | Mantelle | 514/772 |
| 5,492,937 | 2/1996 | Bogentoft et al. | 514/781 |
| 5,540,853 | 7/1996 | Trinh et al. | 510/101 |

FOREIGN PATENT DOCUMENTS

| | | |
|---|---|---|
| 0 104 037 | 3/1984 | European Pat. Off. . |
| 0104037 | 3/1984 | European Pat. Off. . |
| 0271332 | 6/1988 | European Pat. Off. . |
| 0272045 | 6/1988 | European Pat. Off. . |
| 0 474 126 A1 | 3/1992 | European Pat. Off. . |
| 0474126 | 3/1992 | European Pat. Off. . |
| 0 271 332 B1 | 9/1993 | European Pat. Off. . |
| 0 272 045 B1 | 10/1993 | European Pat. Off. . |
| 0 319 555 B1 | 1/1992 | Germany . |
| 61-18716 | 1/1986 | Japan . |
| WO9115210 | 10/1991 | WIPO . |
| WO 92/18133 | 10/1992 | WIPO . |
| WO 93/05032 | 3/1993 | WIPO . |
| WO9413257 | 6/1994 | WIPO . |
| WO 95/11000 | 4/1995 | WIPO . |
| WO 96/11710 | 4/1996 | WIPO . |
| WO 96/14823 | 5/1996 | WIPO . |

*Primary Examiner*—Jose' G. Dees
*Assistant Examiner*—Michael A. Williamson

[57] ABSTRACT

Entirely anhydrous topical preparations comprising (I) propylene carbonate, (II) one or more short carbon-chain alcohols and/or glycols including ethanol, isopropyl alcohol, propylene glycol, butylene glycol, polyethylene glycol, hexylene glycol, methoxypolyethylene glycol, and (III) either or both of glycerol and one or more therapeutically or cosmetically active ingredients.

23 Claims, 5 Drawing Sheets

COMPOSITION BASE FOR TOPICAL THERAPEUTIC AND COSMETIC PREPARATIONS

FIELD OF THE INVENTION

The present invention relates in general to carrier systems for topically applied drugs and cosmetics and, more particularly, to composition bases for topical therapeutic and cosmetic preparations.

BACKGROUND OF THE INVENTION

Consumer demand has recently spurred a proliferation of clear and colorless or "dye-free" products in the marketplace including, among others, liquid soaps, detergents and waxes, shampoos, hair sprays, cosmetics, deodorants, topical medications, beverages, parenteral alimentation solutions and orally ingestible pharmaceutical solutions. Consistent with this demand, the present invention proposes the use of propylene carbonate as a primary solvent in entirely anhydrous, clear and colorless composition bases or carriers systems for topical therapeutic and cosmetic preparations.

Many patent disclosures and other publications have described the use of propylene carbonate in pharmaceutical or cosmetic preparations. Additionally, some commercially available topically applied pharmaceuticals include propylene carbonate as a formulation constituent. For example, propylene carbonate has been used as a solvent in an ointment containing a topical steroid, fluocinolone acetonide (LIDEX®). U.S. Pat. No. 4,017,615 and Published European Patent Application 0 474 126 describe pharmaceutical ointment preparations. "Ointment" is generally defined in pharmaceutical science as a topical preparation containing medicament and petrolatum gel or fatty acids, as well as some cosolvents and penetration enhancers. Ointment has a greasy feel and is usually occlusive when applied to skin.

Other references, Published Japanese Patent Application Nos. 59-70612 and 59-190912, International Patent Publication Nos. WO 91/15210 and WO 94/13257, Published European Patent Specification 0 104 037 and U.S. Pat. No. 4,393,076, disclose topical gels, creams, lotions or solutions comprising water, propylene carbonate as a cosolvent and/or penetration enhancer, and other pharmaceutical excipients. Propylene carbonate is known to decompose in the presence of water into propylene glycol and carbon dioxide. However, carbon dioxide gas generation presents a physical stability problem inasmuch as a closed package tube containing the topical product may burst due to the pressure build-up from the accumulation of the carbon dioxide gas.

Propylene carbonate has also been disclosed for use in connection with film-forming formulations intended for therapeutic and cosmetic applications. For example, U.S. Pat. No. 4,963,591 discloses cosmetic compositions containing ethylcellulose as a film-forming agent and solvents including alcohol and propylene carbonate. The compositions form a curable, water-insoluble, occlusive film upon application to skin. And, European Patent No. 0 319 555 describes a pharmaceutical composition containing film-forming polymers, i.e., a vinylpyrrolidone-vinylacetate copolymer and polymethacrylic acid-butylester, and a mixture of solvents including propylene carbonate. This composition is also intended for transdermal therapeutic application, and will cure to form a flexible film when applied to skin. Regardless of the thinness, flexibility and other characteristics which are intended to enhance their appeal, many consumers nevertheless find such film-forming products to be uncomfortable and even unpleasant because of their occlusive nature.

Published European Patent Specification No. 0 271 332 discloses a composition saturated with a drug for forming a supersaturated composition when applied to a water-wetted area of human skin. This composition contains from 0.1 to 0.5% Klucel as anti-nucleating agent and a mixture of solvents including propylene carbonate, propylene glycol and ethanol. The composition thus requires supplemental water to perform its intended function. Further, it may also contain up to 50% water as a formulation constituent. Published European Patent Specification 0 272 045 describes a two-phase pharmaceutical composition for topical application. Prior to application, two parts must be mixed to form a composition containing a supersaturated drug. U.S. Pat. No. 4,820,724 discloses a dual phase solvent carrier system for topical drug application. The disclosed composition contains actives, a delivery solvent (e.g., benzyl alcohol, propylene carbonate, etc.) comprising about 5 to about 15 weight percent of the composition, and a fugitive solvent (e.g., various volatile alcohols) comprising about 75 to about 95 weight percent of the composition. U.S. Pat. No. 3,899,578 describes topical griseofulvin compositions comprising a solution, a gel, an anhydrous ointment, a paste or an emulsion of the drug in a solvent (e.g., benzyl alcohol, dimethyl phthalate, propylene carbonate and eugenol) and other pharmaceutical excipients. Published Japanese Patent Application No. 61-18716 discloses a tolnaftate gel produced by adding a powder of carboxyvinyl polymer gelation agent to and suspending it in a propylene carbonate solution of tolnaftate and any other medicinally active drugs. A lower alcohol such as ethanol or methanol is then added to dissolve the carboxyvinyl polymer. Then, a glycol (such as propylene, butylene, or hexylene glycol) and water are added. The glycol is believed to be added in order to assist in dissolution of the carboxyvinyl copolymer, thereby enhancing gelation of the composition. Lastly, an organic amine is added to neutralize the carboxyvinyl copolymer and gelation is effected.

A specific yet typical use contemplated by the composition base or "vehicle" formulations manufactured in accordance with the prior art as well as the present invention is as a carrier system for delivery of topical therapeutic products. For example, there are currently many topical antifungal products in the over-the-counter market which enable patients to self-treat athlete's foot, ringworm and jock itch. Although effective when properly used, most of these products require an application frequency of twice a day or more and 2 to 4 week treatment duration. Many persons find such continual attention to their treatment to be unduly burdensome. Consequently, many patients prematurely stop the treatment soon after the apparent symptom of itchiness has been alleviated. In this connection, it is believed that high relapse rates observed in patients suffering from these skin disease treatments are related to the noncompliance of patients to such cumbersome treatment regimens. A need exists, therefore, to develop more efficacious antifungal products which can reduce dosing frequency and/or treatment duration to assure a better therapeutic end result through increased treatment compliance.

A seemingly simple solution to patient compliance problems would be to increase the strength or dosage of the antifungal active ingredients in the formulation and thereby reduce application frequency. However, the use of more potent antifungal drugs is frequently not a viable approach. This is particularly true for patient self-directed treatments because of the potentiality for drug toxicity and other side effects such as skin irritation and sensitization. In self-applied topical therapeutic products, therefore, it would be much more desirable to employ antifungal drugs at conventional "over-the-counter" strengths in an improved carrier formulation to make drug delivery more efficacious. For example, the formulation should enhance the rate of drug penetration into the skin and mucosa tissues and prolong the drug retention in the fungus-residing superficial skin tissues, i.e., the stratum corneum and the epidermis in general. In addition, patient compliance with the treatment would be further promoted if such a product also would possess appealing cosmetic attributes and skin feel.

SUMMARY OF THE INVENTION

The present invention provides an entirely anhydrous composition base (which is also interchangeably referred to herein as a vehicle or carrier system) which can be used to prepare topical drug formulations including, without limitation, antifungal compositions for skin and nail treatment. The carrier system may be manifested, for example, as a gel, a roll-on solution, or an aerosol or pump spray. The base operates in such a manner that active compounds incorporable into the base can penetrate into skin rapidly and remain in the stratum corneum and the epidermis in general for prolonged periods. Topical product formulations comprising a base composed in accordance with the present invention have demonstrated chemical stability sufficient to establish a two-year shelf life and physical stability sufficient to remain in a single, non-crystalline phase for the expected service lives of the products under the normal usage conditions. Furthermore, the formulations have excellent cosmetic attributes, such as good spreadability and skin feel and, especially in the case of glycerol-containing embodiments thereof, moisturizing effect.

Another of the many possible applications of the carrier system of the present invention is as a vehicle for cosmetic preparations. Exemplary cosmetic products may include those having certain active ingredients, such as retinol and alpha-hydroxy acids, which are intended to accelerate the skin tissue renewal process, thus imparting certain cosmetic benefits, e.g., rejuvenation of skin, removal/reduction of wrinkles, and elimination of skin hyperpigmentation (age spots).

Accordingly, the present invention describes entirely anhydrous preparations comprising (I) propylene carbonate, (II) one or more short carbon chain alcohols and/or glycols including ethanol, isopropyl alcohol, propylene glycol, butylene glycol, hexylene glycol polyethylene glycol, methoxypolyethylene glycol and their derivatives, and (III) either or both of glycerol and one or more therapeutically or cosmetically active ingredients.

In the event one or more active ingredients are provided, the propylene carbonate functions as the primary solvent and the alcohol and/or glycol functions as a secondary solvent (or cosolvent) for such ingredients. In circumstances where glycerol is provided, the alcohol and/or glycol promotes mixability of the propylene carbonate and glycerol, which constituents are otherwise immiscible. Moreover, when present, glycerol offers the considerable benefit of skin moisturization regardless of whether it is employed with or without other medicinally or cosmetically active ingredients. Hence, glycerol (or glycerine) may be viewed as an additional species of "active" ingredient suitable, and frequently preferred, for use in the carrier system of the present invention.

When one or more active ingredients are included in the formulation, mixtures of these components, in proper concentration, may produce a "single-phase" or "one-phase" preparation with the actives being completely dissolved in the formulation. Although not generally emphasized in the context of the present invention, pigmented, translucent or even opaque compositions may be developed which incorporate the essential components of the instant clear and colorless carrier system. For example, a translucent product may be formed when the active ingredient content exceeds that which can be dissolved by the aforementioned solvents. Similarly, certain actives, pigments or other ingredients may be added to the clear base composition to effectuate desired levels of translucence or even opacity when such may be preferable to the consuming public in respect to the aesthetics expected of certain consumer products.

The instant anhydrous base composition provides: fast skin absorption of the active(s), prolonged retention of the active(s) in the stratum corneum and the epidermis in general, excellent cosmetic appearance/aesthetics, non-greasy feel when applied to skin, physical stability, i.e., no phase separation or crystallization during storage, and minimal or no skin and mucosa irritation. The carrier system may also comprise gelling agents such as cellulose ethers (e.g., Klucel®), polyvinylpyrrolidone (Povidone®) carboxyvinyl polymer (HIVIS 105®) and the like in order to thicken the composition to a desired gel consistency.

As will be described in greater detail hereinafter, comparative studies have shown that a 2% miconazole nitrate clear gel formulated according to the instant invention exhibits superior drug penetration into the stratum corneum and the epidermis in general when compared to a miconazole nitrate cream of identical active strength. Moreover, primary dermal irritation tests conducted in rabbits indicate that clear gel formulations of 2% miconazole nitrate formulated as described herein are essentially non-irritating to skin. Indeed, a representative 2% miconazole nitrate clear gel formulation according to this invention has been shown to be even milder than a commercially available 2% miconazole cream product for skin fungal infections.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings wherein.

DETAILED DESCRIPTION OF THE INVENTION

Figure 1:
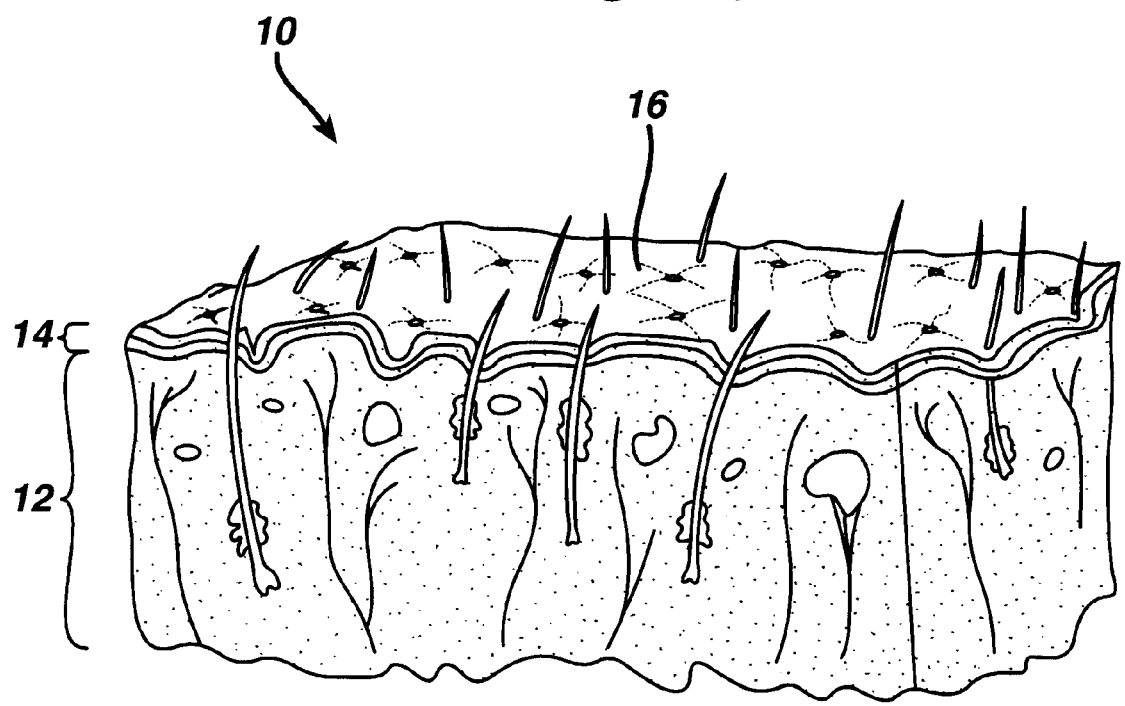
FIG. 1 is an elevational cross-section view of the dermis and epidermis of human skin.

Referring to FIG. 1, there is shown a portion of human integument or skin 10, in particular the dermis 12 and epidermis 14. The dermis is disposed interiorly of the epidermis and consists principally of dense connective tissue, elastic fibers, small muscles, hair follicles, sudoriferous (sweat) and sebaceous glands, and blood vessels. The epidermis 14 is nonvascular and covers the dermis 12. It is comprised of several layers or strata named according to various properties associated with each layer such as the shape of cells, texture, composition and position. The outermost of these layers, the stratum corneum 16, is composed of plates which are fused together and contain the fibrous protein keratin. The plates are the remains of the cells of underlying strata of the epidermis. The stratum corneum sloughs off or desquamates and is thickest on the palms of the hands and soles of the feet. It is in the epidermis tissues generally, including the stratum corneum, that many skin diseases reside.

The present invention describes entirely anhydrous preparations comprising (I) propylene carbonate, (II) one or more short carbon chain alcohols and glycols including ethanol, isopropyl alcohol, propylene glycol, butylene glycol, hexylene glycol polyethylene glycol, methoxypolyethylene glycol and their derivatives, and (III) either or both of glycerol and one or more therapeutically or cosmetically active ingredients.

The instant anhydrous formulations employ propylene carbonate as the primary solvent for the active ingredients because of its considerable solubilization properties. It is also non-toxic, non-greasy, and non-irritating, even at very high concentrations. Moreover, because propylene carbonate reacts with water, releasing carbon dioxide gas and causing stability problems, the entirely anhydrous formulations of the present invention prevent the degradation of propylene carbonate during storage.

In the event one or more active ingredients are provided, the propylene carbonate functions as a primary solvent and the alcohol and/or polyol functions as a secondary solvent for such ingredients. In circumstances where glycerol is provided, the alcohol and/or glycol promotes mixability of the propylene carbonate and glycerol, which constituents are otherwise immiscible. Moreover, when present, glycerol offers the recognized benefit of skin moisturization whether employed with or without other medicinally or cosmetically active ingredients. When an agent such as a volatile alcohol is chosen as a cosolvent, the skin moisturizing effect of glycerol is especially advantageous because it counteracts the tendency of the alcohol to over-dry the skin. Hence, glycerol (or glycerine) may therefore be viewed as an additional species of "active" ingredient suitable, and frequently preferred, for use in the carrier system of the present invention. In addition, urea, a recognized keratin softener and moisturizer, may also be provided as a supplemental moisturizing agent. Although urea is essentially insoluble in propylene carbonate and slightly soluble in the cosolvents mentioned herein, it is highly soluble in glycerol and tends to augment glycerol's moisturization effect.

When one or more active ingredients are incorporated into the formulation, mixtures of these components, in proper concentrations, produce a single-phase preparation with the actives being completely dissolved in the formulation.

According to at least one presently preferred embodiment, the anhydrous base composition according to the instant invention can be used to prepare a topical drug formulation including, without limitation, an antifungal composition for skin and nail treatment.

The active ingredients or compounds for such preparations preferably comprise antifungal drugs such as imidazoles, azoles and other types of antifungal drugs (e.g., miconazole nitrate, econazole nitrate, itraconazole, saperconazole, oxyconazole, sufaconazole, clotrimazole, terbinafine, amorolfine, fluconazole, ketoconazole and terconazole).

The carrier system formulation according to the present invention may include other active ingredients including, without limitation, and in any compatible combination, sunscreens, sunblocks, anti-inflammatory agents, antioxidants/radical scavengers, chelators, retinoids, benzofuran derivatives, N-acetyl-L-cysteine and derivatives thereof, skin protectants, and vitamins.

Suitable sunscreening agents may include, for example: p-aminobenzoic acid, its salts and its derivatives (ethyl, isobutyl, glyceryl esters; p-dimethylaminobenzoic acid and its esters); anthranylates (i.e., o-aminobenzoates; methyl, menthyl, phenyl, benzyl, phenylethyl, linalyl, terpinyl, and cyclohexenyl esters); salicylates, (amyl, phenyl, benzyl, menthyl, glyceryl, and dipropyleneglycol esters); cinnamic acid derivatives (methyl and benzyl esters, α-phenyl cinnamonitrile, butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophanone; naphthol-sulfonates (sodium salts of 2-naphthol-3,6-disulfonic and of 2-naphthol-6,8-disulfonic acids); dihydroxynaphthoic acid and its salts; o- and p-hydroxybiphenyldisulfonates; coumarin derivatives (7-hydroxy, -7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline and its derivatives (8-hydroxyquinoline salts, 2-phenylquinoline); uric and vilouric acids; tannic acid and its derivatives (e.g., hexaethylether; (butyl carbotol) (6-propyl piperonyl)ether; hydroquinone; hydroxy- or methoxy-substituted benzophenones and the benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone); 4-isopropyldibenzoylmethane, butylmethoxydibenzoylmethane; etocrylene; and 4-isopropyl-dibenzoylmethane.

Preferred sunscreens useful in the compositions of the present invention are 2-ethylhexyl-p-methoxycinnamate, butyl-methoxydibenzoylmethane, 2-hydroxy-4-methoxybenzophenone, octyldimethyl-p-aminobenzoic acid and mixtures thereof.

Suitable steroidal anti-inflammatory agents may include, although are not limited to, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and mixtures thereof may be used. The preferred steroidal anti-inflammatory for use in the present invention is hydrocortisone.

A second class of anti-inflammatory agents which is useful in the compositions of the present invention includes the nonsteroidal anti-inflammatory agents. The variety of compounds encompassed by this group are well-known to those skilled in the art. For detailed disclosure of the chemical structure, synthesis side effects, etc., of nonsteroidal anti-inflammatory agents, reference may be had to standard texts, including *Antiinflammatory and Anti-Rheumatic Drugs*, K. D. Rainsford, Vol. I–III, CRC Press, Boca Raton, (1985), and *Anti-inflammatory Agents*, Chemistry and Pharmacology, 1, R. A. Scherrer, et al., Academic Press, New York (1974).

Suitable non-steroidal anti-inflammatory agents useful in the compositions of the present invention include, but are not limited to:

1) the oxicams, such as piroxicam, isoxicam, tonexicam, sudoxicam, and CP-14,304;
2) the salicylates, such as salicylic acid, aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;
4) the fenamates, such as mefenamic, meclofenamic, flufenamic, niflumic, and tolfenamic acids;
5) the propionic acid derivates, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and
6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, stofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred with ibuprofen, naproxen, and flufenamic acid being most preferred.

Another class of anti-inflammatory agents which are useful in the present invention are the anti-inflammatory agents disclosed in U.S. Pat. No. 4,708,966, the disclosure of which is incorporated herein by reference. That patent discloses a class of nonsteroidal anti-inflammatory compounds which comprise specifically substituted phenyl compounds, especially substituted 2,6-di-tert-butyl phenol derivatives. For example, compounds selected from 4-(4'pentyn-3'-one)-2,6-di-t-butylphenol; 4-(5'-hexynoyl)-2,6-di-t-butylphenol, 4-((S)-(–)-3'-methyl-5'hexynoyl)-2,6-di-t-butylphenol, 4-((R)-(+)-3'-methyl-5'-hexynoyl)-2,6-di-t-butylphenol; and 4-(3',3'-dimethoxypropionyl)-2,6-di-t-butylphenol are useful in the present invention.

Yet another class of anti-inflammatory agents which are useful in the present invention are those disclosed in U.S. Pat. No. 4,912,248, the disclosure of which is incorporated herein by reference. This patent discloses compounds and diastereomeric mixtures of specific 2-naphthyl-containing ester compounds, especially naproxen ester and naproxol ester compounds, having two or more chiral centers.

Additionally, so-called "natural" anti-inflammatory agents are useful in the present invention. For example, candelilla wax, alpha bisabolol, aloe vera, Manjistha (extracted from plants in the genus Rubia, particularly *Rubia cordifolia*), and Guggal (extracted from plants in the genus Commiphora, particularly *Commiphora mukul*, may be used.

Suitable anti-oxidants/radical scavengers may include ascorbic acid (vitamin C) and its salts, tocopherol (vitamin E), and its derivatives such as tocopherol sorbate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, amino-guanidine), sulfhydryl compounds (e.g., glutathione), and dihydroxy fumaric acid and its salts may be used, as well as EDTA, BHT and the like.

In a wrinkle and atrophy regulating composition, the present invention may include a chelating agent as an active agent alone or in combination with other active compounds. As used herein, "chelating agent" means an active agent capable of removing a metal ion from a system by forming a complex so that the metal ion cannot readily participate in or catalyze chemical reactions. The inclusion of a chelating agent increases the wrinkle regulating benefits of the composition.

A safe and effective amount of a chelating agent may be added to the compositions of the present invention, preferably from about 0.1% to about 10%, more preferably from about 1% to about 5%, of the composition. Chelators useful in compositions of the present invention are disclosed in U.S. Pat. No. 5,487,844. Preferred chelators useful in compositions of the present invention are furildioxime and derivatives thereof, more preferably amphi-2-furildioxime.

A wrinkle and atrophy regulating composition of the present invention may also include a retinoid, preferably retinoic acid, as an active agent either alone or in addition to other active compounds. The inclusion of a retinoid increases the wrinkle regulating benefits of the composition. A safe and effective amount of a retinoid may be added to the compositions of the present invention, preferably from about 0.001% to about 2%, more preferably from about 0.01% to about 1% of the composition. As used herein, "retinoid" includes retinol, retinoic acid, isotretinoin retinyl palmitate and retinyl esters, as well as all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

Cosmetic products formulated according to the present invention may also include alpha-hydroxy acids, which, like retinoids, are intended to accelerate the skin tissue renewal process, thus imparting certain cosmetic benefits such as rejuvenation of skin, removal/reduction of wrinkles, and elimination of skin hyperpigmentation (age spots).

Similarly, wrinkle and atrophy regulating compositions according to the present invention may also comprise a benzofuran derivatives, preferably amiodarone, as an active agent either alone or in combination with other active compounds. Inclusion of a benzofuran derivative increases the wrinkle regulating benefits of the composition.

Additional active and inactive ingredients may also include, without limitation, local analgesics such as benzocaine, menthol, and the like (wherein menthol is also capable of providing a soothing, cooling sensation), as well as emollients, antihistamines, fragrances, thickeners and preservatives other than those already listed.

The carrier system may also comprise, when desired, a suitable gelling agent including, but not limited to, cellulose esters such as hydroxypropyl cellulose (Klucel®), hydroxyethyl cellulose (Natrosol®), polyvinylpyrrolidone (Povidone®), carboxyvinyl polymer (HIVIS 105®) and the like that may be provided in any amount necessary to thicken the composition to a desired gel consistency. When formulated as a gel, the base composition exhibits favorable spreadability characteristics. In addition, it remains visible on the skin surface longer, thereby instilling in the user the impression that the vehicle is more completely delivering its active ingredient(s).

The carrier system may also comprise antiseptics such as tea tree oil, as well as antibiotics including, without limitation, neomycin sulfate, polymixin B sulfate, bacitracin, ofloxaxin, erythromycin, clindamycin, nupirocin and oxytetracycline HCL.

Additionally, and although not generally emphasized in the "clear and colorless" context of the present invention, pigmented, translucent or even opaque compositions may be developed which incorporate the essential components of the instant carrier system. For example, a translucent product may be formed when the active content exceeds that which can be dissolved by the aforementioned solvents. Similarly, certain actives, pigments or other ingredients may be added to the clear base composition to effectuate desired levels of pigmentation, translucence or even opacity when such may be customary or preferable to the consuming public in respect to the aesthetics expected of certain topically applied therapeutic or cosmetic products.

In this regard, further examples of ingredients which may be added to affect the aesthetics of the carrier system include zinc oxide or titanium oxide as insoluble sunscreening agents which may be provided as needed to achieve any desired level of translucence, sunscreening effectiveness and/or therapeutic benefits. Likewise, corn starch (a moisture absorber) and baking soda (a deodorant) may also be added to the composition to bring about certain degrees of translucence. In the case of antifungal compositions for athlete's foot, baking soda may be a particularly desirable additive. Based on formulation needs, the acidity and alkalinity can be adjusted by adding sodium hydroxide, potassium hydroxide, salicylic acid, alpha-hydroxy acid, etc.

TABLE 1 sets forth the skin moisturization effect test data of several topical therapeutic products (Products 1, 2 and 3) formulated according to the present invention at two hours after application to the skin of a human subject. TABLE 1 also includes the corresponding test data of other topically applied products, one being a topical therapeutic product (Product 4) having the identical active ingredient in the identical concentration as Products 1 through 3. Product 5 is a designated skin moisturizing product, Neutrogena® Emulsion, Norwegian Formula, a product of Neutrogena Corp., a subsidiary of Johnson & Johnson, New Brunswick, N.J. Product 6 is not a product but rather an adjacent untreated area of skin to be used as a study control site.

Figure 2:
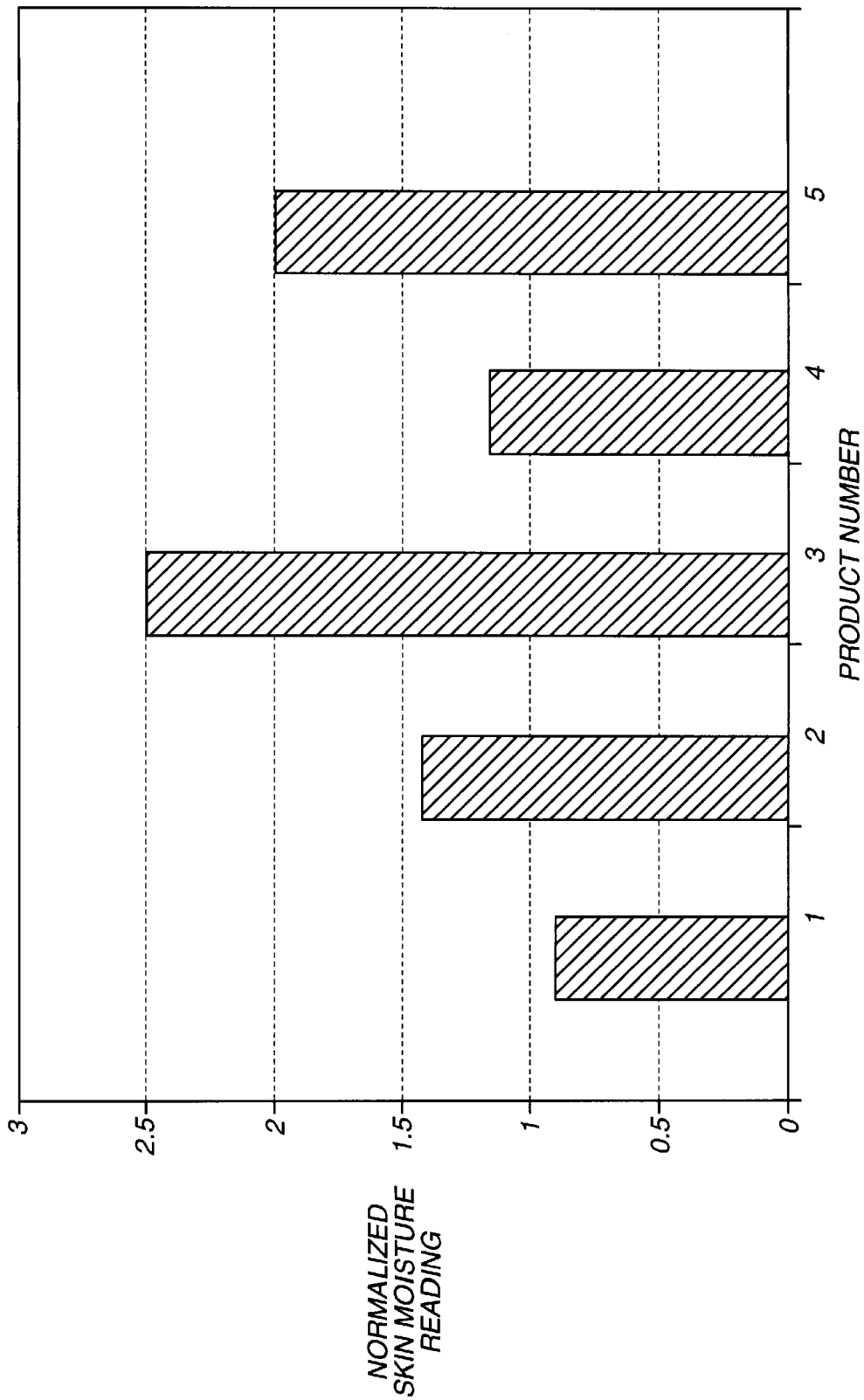
FIG. 2 is a bar graph depicting the skin moisturization effect of several topical therapeutic products formulated according to the present invention versus other topically applied products at two hours after application of the products to human skin.

The method chosen for measuring skin moisturization involved measurement of skin impedance in ambient conditions of 22° C. temperature and 33% relative humidity. The test involved an adult human male (Subject 1) and an adult human female (Subject 2). Each subject was measured at six test sites on each ventral forearm respectively disposed in increasing number and increasing distance from the distal end of the forearm. Each test site was one inch in diameter (5.067 $cm^2$) and 0.3 ml of sample was applied using a template and spread evenly with a Rainin pipet. Skin impedance was measured at two hours after product application using a commercially available skin moisture analyzer, NOVA DPM9003, interfaced with a Compaq 2 personal computer which together convert measured skin impedance in ohms to a dimensionless relative moisturization value (DPM Reading). The DPM Reading for each site is then converted to a Normalized Reading by dividing the DPM reading for the site by the DPM Reading of the untreated control test site number 6. The four Normalized Readings for each test site are then averaged. It is the average Normalized Readings for each of test sites 1 though 5 (corresponding to Products 1 through 5) which are reflected in FIG. 2. The formulations for each of Products 1 through 4 are as follows. The formulation for Neutrogena® Emulsion, Norwegian Formula contains 25% glycerine, other emollients and water.

Product 1:

2 weight percent (wt %) miconazole nitrate 20 wt % propylene carbonate 20 wt % propylene glycol 55.87 wt % ethanol 0.05 wt % butyl hydroxy toluene (BHT)

0.08 wt % menthol 2 wt % Klucel HF®

Product 2:

2 wt % miconazole nitrate 20 wt % propylene carbonate 10 wt % propylene glycol 10 wt % glycerol 55.87 wt % ethanol 0.05 wt % BHT 0.08 wt % menthol 2 wt % Klucel HF®

Product 3:

2 wt % miconazole nitrate 20 wt % propylene carbonate 20 wt % glycerol 55.87 wt % ethanol 0.05 wt % BHT 0.08 wt % menthol 2 wt % Klucel HF®

Product 4:

2 wt % miconazole nitrate 2 wt % Arlamol E® (emollient)

20 wt % propylene carbonate 20 wt % propylene glycol 53.87 wt % ethanol 0.05 wt % BHT
0.08 wt % menthol
2 wt % Klucel HF®

TABLE 1

TWO HOUR SKIN MOISTURIZATION EFFECT

| Product/ | | DPM Reading | | Normalized Reading | | Average Normalized |
|---|---|---|---|---|---|---|
| Test Site | Subject | L. arm | R. arm | L. arm | R. arm | Reading |
| 1 | 1 | 124 | 168 | 0.83 | 1.14 | 0.90 |
|   | 2 | 108 | 124 | 0.68 | 0.97 |  |
| 2 | 1 | 241 | 192 | 1.61 | 1.30 | 1.42 |
|   | 2 | 144 | 240 | 0.91 | 1.88 |  |
| 3 | 1 | 352 | 372 | 2.35 | 2.51 | 2.51 |
|   | 2 | 352 | 380 | 2.23 | 2.97 |  |
| 4 | 1 | 172 | 144 | 1.15 | 0.97 | 1.16 |
|   | 2 | 186 | 174 | 1.18 | 1.36 |  |
| 5 | 1 | 278 | 256 | 1.85 | 2.24 | 2.03 |
|   | 2 | 354 | 292 | 2.24 | 2.28 |  |
| 6 | 1 | 150 | 148 | 1.00 | 1.00 | 1.00 |
|   | 2 | 158 | 128 | 1.00 | 1.00 |  |

TABLE 2

FIVE HOUR SKIN MOISTURIZATION EFFECT

| Product/ | | DPM Reading | | Normalized Reading | | Average Normalized |
|---|---|---|---|---|---|---|
| Test Site | Subject | L. arm | R. arm | L. arm | R. arm | Reading |
| 1 | 1 | 128 | 134 | 1.03 | 1.16 | 1.05 |
|   | 2 | 108 | 100 | 1.02 | 1.00 |  |
| 2 | 1 | 174 | 198 | 1.40 | 1.71 | 1.59 |
|   | 2 | 140 | 192 | 1.32 | 1.92 |  |
| 3 | 1 | 356 | 376 | 2.87 | 3.24 | 2.98 |
|   | 2 | 296 | 300 | 2.79 | 3.00 |  |
| 4 | 1 | 152 | 124 | 1.23 | 1.07 | 1.15 |
|   | 2 | 118 | 120 | 1.11 | 1.20 |  |
| 5 | 1 | 332 | 346 | 2.68 | 2.98 | 3.10 |
|   | 2 | 392 | 304 | 3.70 | 3.04 |  |
| 6 | 1 | 124 | 116 | 1.00 | 1.00 | 1.00 |
|   | 2 | 106 | 100 | 1.00 | 1.00 |  |

TABLE 3

SEVEN HOUR SKIN MOISTURIZATION EFFECT

| Product/ | | DPM Reading | | Normalized Reading | | Average Normalized |
|---|---|---|---|---|---|---|
| Test Site | Subject | L. arm | R. arm | L. arm | R. arm | Reading |
| 1 | 1 | 100 | 124 | 0.77 | 1.03 | 0.95 |
|   | 2 | 102 | 100 | 1.02 | 0.96 |  |
| 2 | 1 | 128 | 158 | 0.98 | 1.32 | 1.37 |
|   | 2 | 130 | 196 | 1.30 | 1.88 |  |
| 3 | 1 | 312 | 356 | 2.40 | 2.97 | 2.64 |
|   | 2 | 260 | 270 | 2.60 | 2.60 |  |
| 4 | 1 | 134 | 120 | 1.03 | 1.00 | 1.05 |
|   | 2 | 108 | 112 | 1.08 | 1.08 |  |
| 5 | 1 | 328 | 324 | 2.52 | 2.70 | 2.89 |
|   | 2 | 348 | 296 | 3.48 | 2.85 |  |
| 6 | 1 | 130 | 120 | 1.00 | 1.00 | 1.00 |
|   | 2 | 100 | 104 | 1.00 | 1.00 |  |

Figure 3:
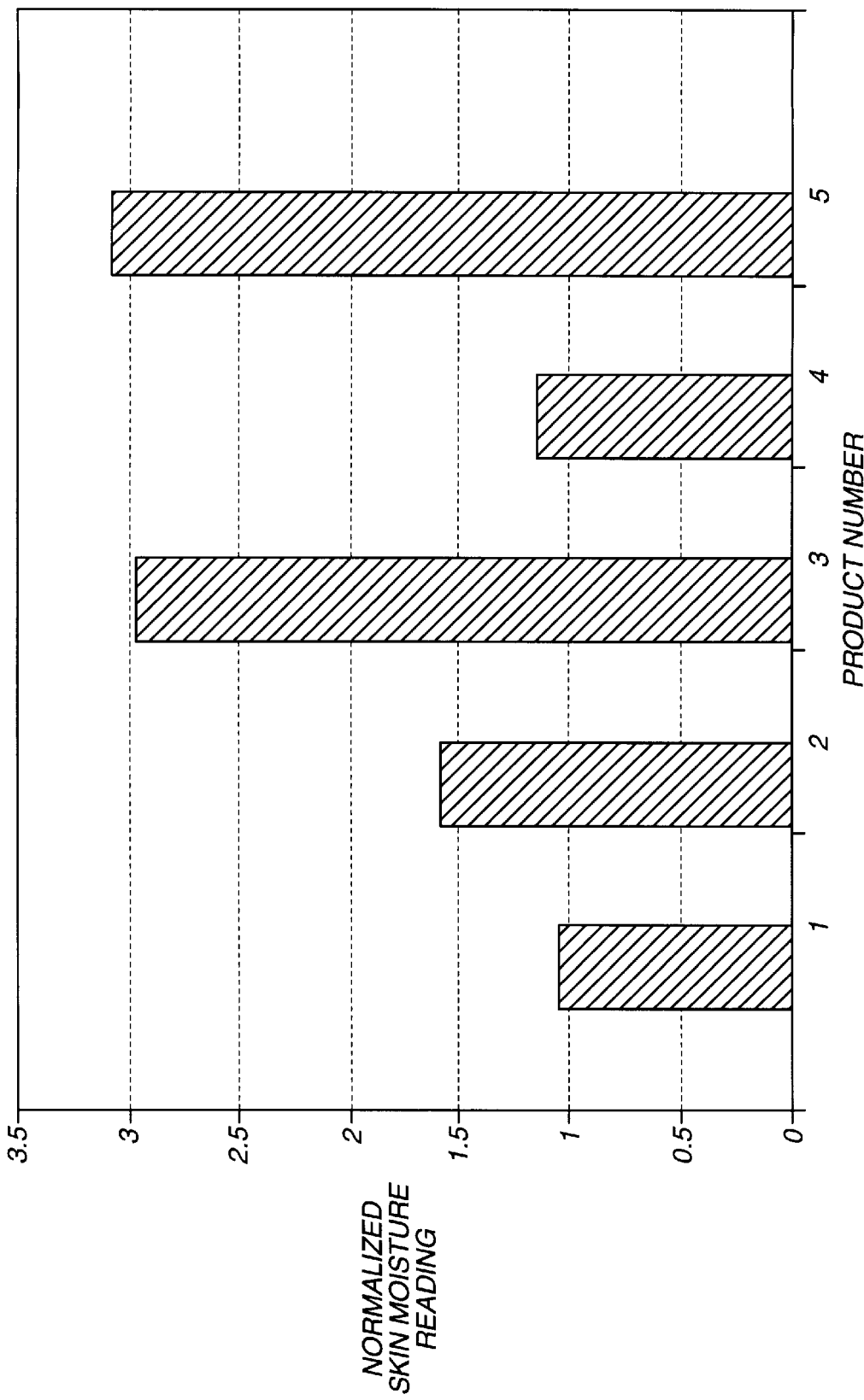
FIG. 3 is a bar graph depicting the skin moisturization effect of several topical therapeutic products formulated according to the present invention versus other topically applied products at five hours after application of the products to human skin.
Figure 4:
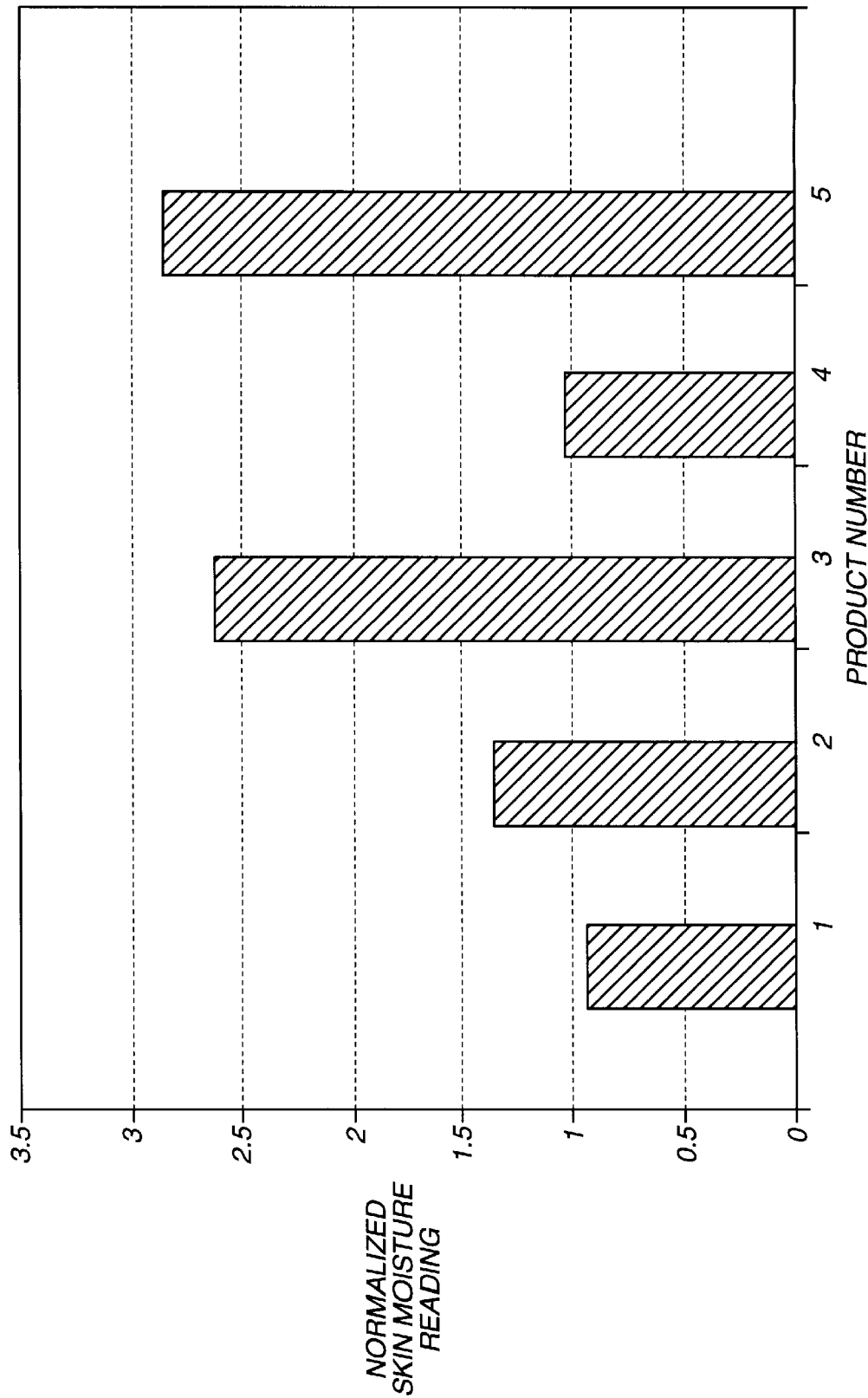
FIG. 4 is a bar graph depicting the skin moisturization effect of several topical therapeutic products formulated according to the present invention versus other topically applied products at seven hours after application of the products to human skin.

TABLE 2 and FIG. 3 represent the skin moisturization effect of Products 1 though 5 as measured five hours after application, and TABLE 3 and FIG. 4 reflect the skin moisturization effect of those products seven hours after application. In all other respects, including test protocol and product formulations, the tests which produced the information provided in TABLES 2 and 3 and FIGS. 3 and 4 were identical to those of FIG. 2 and TABLE 1. Generally, topical formulations containing more than 25% ethanol produce a skin-drying effect. Surprisingly, however, Products 1 and 4 containing more than 55% ethanol and no glycerol did not exhibit any skin-drying effect. TABLES 1 through 3 and FIGS. 2 through 4 also reveal that therapeutic products formulated in accordance with the present invention demonstrate increased capacity to moisturize skin as their glycerol contents are increased. In addition, Product 3 (a 20% glycerol, 55% ethanol, no emmolient composition) unexpectedly exhibits a skin moisturization effect comparable to, and at two hours after application superior to Product 5, a designated skin moisturizing product, i-e. Neutrogena® Emulsion, Norwegian Formula (a 25% glycerol, water and emollient composition).

Although Products 1 through 3 contain up to 20 wt % glycerol, the composition bases and products contemplated by the invention are not so limited. Indeed, certain presently preferred embodiments of the carrier system and/or products formulated pursuant thereto may include up to about 50 wt % glycerol. For instance, in research and development culminating in the present invention, antifungal clear gel compositions have been successfully produced which contain 45 wt % glycerol. Further, 50 wt % glycerol is not an absolute upper limit in therapeutic or cosmetic products that may be manufactured consistent with this invention. However, glycerol contents exceeding about 50 wt % tend to impart to the product a "greasy" type feel normally associated with ointments. To the extent such a sensation is to be avoided, therefore, a formulation limit of approximately 50 wt % glycerol should not be exceeded.

Similarly, the present inventors have prepared anhydrous, single phase therapeutic products containing from less than 1 wt % to over 58 wt % of alcohols as cosolvent. Moreover, although the present inventors have formulated several products according to the invention using approximately 20 wt % propylene carbonate, lesser amounts (e.g., concentrations as low as 5 wt % or less which generally correspond to those often found in cosmetic preparations) and greater amounts (e.g., concentrations greater than 20% and up to nearly 100 wt % as such comparatively high amounts have been recognized in the art as causing only moderate skin irritation) are contemplated to be within the scope of the present invention.

Clear gel Product 1, as formulated above, and an identical strength 2% miconazole nitrate antifungal cream composition not formulated according to the present invention (Product A) were also observed to determine their relative effectiveness in terms of their ability to be absorbed by the skin and their capacity to resist attack by microbiological agents (specifically *Trichophyton rubrum* or, simply, *T. rubrum*). The results of those studies are reproduced in Tables 4 and 5 respectively.

The common characteristics of the protocols of the skin absorption and microbiological agent invasion inhibition tests summarized in Tables 4 and 5 are as follows. Each of the products was applied to the stratum corneum of four different samples of dermatomed cadaver skin from the back of a 71 year old male. The skin samples were placed onto the surface of a buffer-moistened pad for 24 hours, after which the treated surfaces of the samples were cleansed with distilled water and liquid Ivory® soap.

As for the skin absorption test summarized in Table 4, the dermis and the epidermis of the individual samples were separated and the content of the relevant product (in micrograms) absorbed into the epidermis and dermis of a respective skin sample were measured. The four quantitative values of the products measured in each of the epidermis and dermis were then summed and averaged.

TABLE 4

IN VITRO SKIN ABSORPTION OF MICONAZOLE NITRATE
(24-hour results (μg), N = 4)

| Product | Epidermis Avg. | Dermis Avg. |
|---|---|---|
| Product 1 | 30.47 | 7.94 |
| Product A | 8.49 | 7.29 |

Table 4 shows that while the drug concentration in the dermis was substantially the same for both formulations, the concentration of Product 1 in the epidermis was considerably greater than that of Product A. This result would appear to suggest that the anhydrous clear gel formulation of Product 1 may be used to selectively deliver actives to the stratum corneum and the epidermis in general, which are usually the targeted tissues in many skin diseases. And, since more drug is delivered to the epidermis, particularly the stratum corneum, which could serve as a reservoir for prolonged effect, longer retention of the drug in the epidermis can be expected for Product 1. This prolonged and intensified treatment per application of Product 1 may be practically translated into a reduced daily application frequency and a reduction in treatment duration, both of which promote patient compliance with and, ultimately, efficacy of the treatment.

The test protocol underlying the in vitro microbiological agent inhibition test results summarized in Table 5 further included evaluating the antifungal activity of the samples of cadaver skin treated with Product 1 and Product A. A Seeded Agar Plate test is employed whereby agar is seeded with a culture of the fungus, *T. rubrum* (the organism primarily associated with skin fungal infections), poured into a petri dish, allowed to harden and thereafter exposed to cadaver skin samples. More particularly, the epidermis and dermis of each skin sample are separated and the epidermal portions thereof are placed in inverted "face-down" orientation onto the seeded agar dishes whereby the stratum corneum of the samples contacts the cultures of *T. rubrum*. The samples remain on the seeded agar dishes for seven days and are then removed. The fungal inhibitive activity of the products is empirically determined as a function of the size of the area of *T. rubrum* encroachment observed on the treated cadaver skin samples. Conversely, the test may be viewed as the product's capacity to inhibit fungal activity in the treated area. This "zone of inhibition" is measured in millimeters, the averages of the several samples of which are recorded in Table 5 for both the stratum corneum and the underlying epidermal tissues.

TABLE 5

IN VITRO ZONE OF INHIBITION OF *T. RUBRUM* ENCROACHMENT

| | Average Zone of Inhibition (mm) | |
|---|---|---|
| Product | Stratum Corneum | Underlying Epidermal Tissue |
| Product 1 | 20 | 6 |
| Product A | 6 | 0 |

The results of Table 5 clearly show that Product 1, an anhydrous clear gel formulation according to the present invention, exhibits much higher fungistatic activity than a miconazole cream of identical strength which is not composed in accordance with the invention. This finding is fully consistent with and perhaps at least partially explains the skin absorption test results of Table 4, and vice versa.

The chemical stability of Product 1 was also measured against an identical strength, commercially available 2% miconazole nitrate antifungal cream (Product B) which also is not formulated according to the present invention. The products were examined using an "accelerated stability" procedure which included: (1) placing individual samples of the respective product formulation in individual air-tight pharmaceutical packages (e.g., crimped-top glass vials or plastic tubes); (2) placing the formulations in stability chambers at a specified elevated temperature and for a specified duration (in the present instance, 13 weeks at 50° C.); (3) periodically removing the formulations from the stability chambers and analyzing the drug contents thereof using High Performance Liquid Chromatography (HPLC); and comparing the drug content remaining after prolonged exposure at elevated temperatures to determine the chemical stability.

The accelerated stability test revealed that Product 1 remained stable under the prescribed test conditions which translate to a two year shelf life using known linear kinetics of degradation, which shelf life is a required standard for topical therapeutic products. Further, Product 1 remained in a single, non-crystalline phase throughout the accelerated stability test (as well as several freeze-thaw tests) which suggests it will remain physically stable throughout its projected service life.

Lastly, Product 1 and Product B were each tested to determine their Primary Dermal Irritation (PDI) Classifications according to the following scale:

| PDI INDEX | PDI CLASSIFICATION |
|---|---|
| 0.0 | Non-irritant |
| 0.1–2.0 | Mild irritant |
| 2.1–5.0 | Moderate irritant |
| 5.1–8.0 | Severe irritant |

The comparative test involved a Modified Draize Rabbit PDI test wherein fur is clipped from the back and flank of New Zealand White Albino rabbits to expose the underlying skin in those areas. Both intact and abraded skin is tested with each formulation (abrasions were made with a barbed tip of a sterile hypodermic needle to achieve minor incisions only penetrating the stratum corneum). Approximately 0.25 mLs of each product formulation is placed in several Hill Top Chambers® containing Webril® pads. The several samples are secured to the animals' skin with Dermacil® cloth tape. After 24 hours the chamber is removed and the skin test sites are cleansed. Evaluation of the test is performed at at least one hour and at 48 hours following removal of the chambers. Evaluation is by visual inspection and is based upon edema (swelling) and erythema (redness) observed at the test sites, using a score of 1 to 4 (from very slight to very severe). The edema and erythema scores are summed for each site, and average scores for each product are then determined according to the aforementioned PDI Index. Product 1 demonstrated a PDI Index of 2.0 and a PDI Classification as a mild irritant. By comparison, the commercially available Product B manifested a PDI Index ranging from 3.5 to 4.2 (average=3.85) and a PDI Classification as a moderate irritant. Thus, Product 1, a clear, anhydrous gel antifungal composition formulated pursuant to the instant invention, has been shown to be less irritating than a commercially available miconazole nitrate antifungal cream product of identical active strength.

Figure 5:
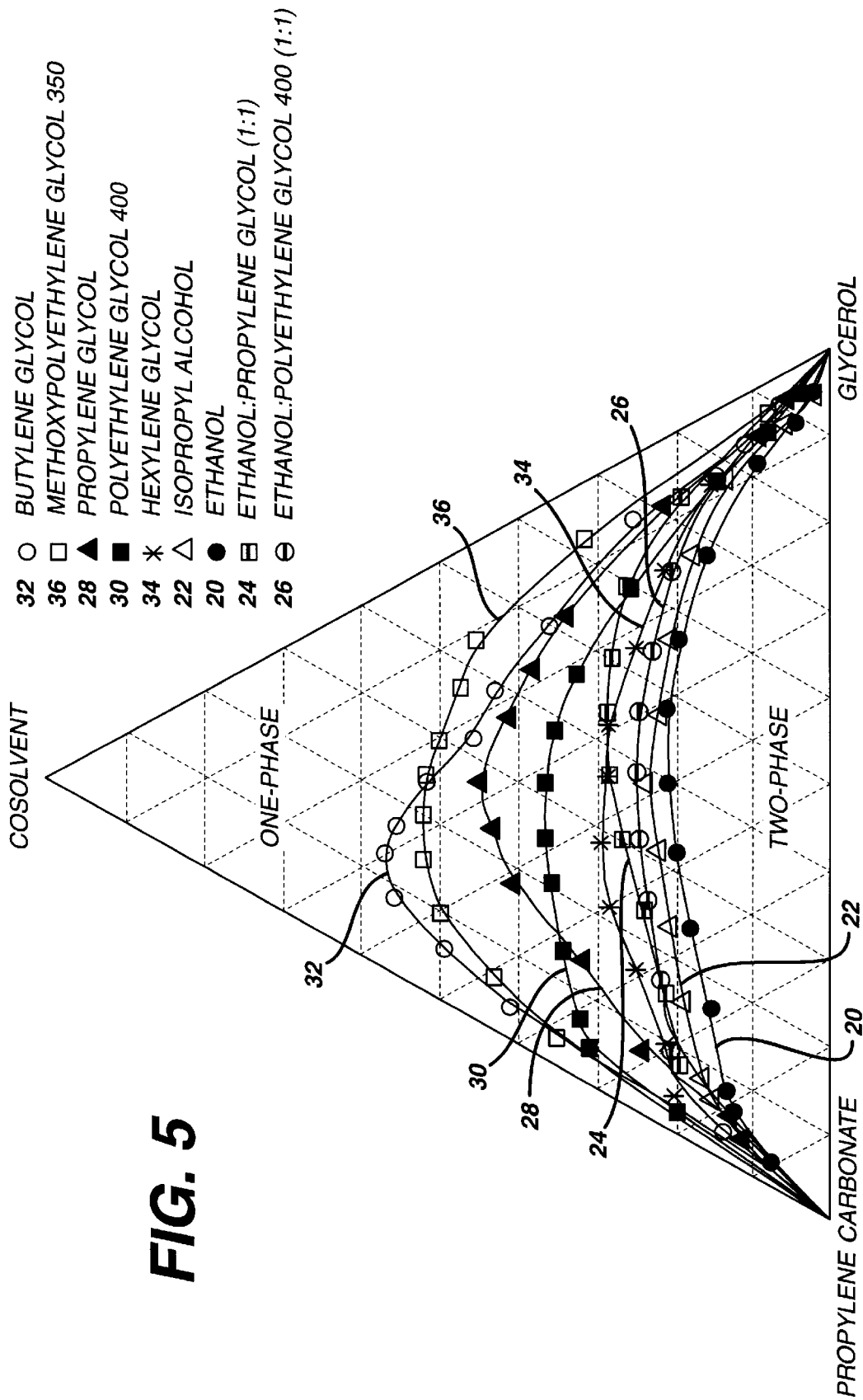
FIG. 5 is a phase diagram demonstrating the requisite quantities of selected alcohols, glycols and alcohol/glycol blends necessary to maintain a single phase composition of propylene carbonate and glycerol.

FIG. 5 is a phase diagram demonstrating the requisite relative quantities of selected alcohol, glycol and alcohol/glycol cosolvents necessary to maintain compositions which also include various relative quantities of propylene carbonate and glycerol in clear and colorless, single-phase states. The data on which the phase diagram of FIG. 5 was based was observed at an ambient temperature of 22° C. The phase diagram defines an equilateral triangle, the lower left and right vertices of which respectively represent compositions containing 100 wt % propylene carbonate and 100 wt % glycerol, whereas the upwardly directed central vertex represents a composition containing 100 wt % of a selected cosolvent. The bases of the triangle opposite the respective vertices represent, as the case may be, compositions containing 0 wt % of either propylene carbonate, glycerol or selected cosolvent. And, lines extending parallel to a particular triangle base line represent, starting at the base line and moving toward the opposite vertex, 10 wt % incremental increases in the content of either the propylene carbonate, glycerol or cosolvent constituent designated by the opposed vertex.

Lines 20, 22, 24, 26, 28, 30, 32, 34 and 36 respectively represent the single-phase/dual-phase separation lines associated with the cosolvents ethanol, isopropyl alcohol, a 1:1 ethanol-propylene glycol blend, a 1:1 ethanol-polyethylene glycol 400 blend, propylene glycol, polyethylene glycol 400 and butylene glycol. Using ethanol as an example, any propylene carbonate, glycerol and ethanol composition containing any quantity of ethanol in the area of the phase diagram above line 20 (i.e., in the direction toward the triangle vertex identified as "cosolvent") will exist as a one-phase system with glycerol being fully dissolved in the propylene carbonate and ethanol. Conversely, any such composition containing any quantity of ethanol in the area of the phase diagram below line 20 will exist as a two-phase system whereby glycerol may be, at best, suspended by but not dissolved in the propylene carbonate and ethanol. A similar analysis may be made in respect to the single-phase/dual-phase separation lines 22 (isopropyl alcohol), 24 (1:1 ethanol-propylene glycol blend), 26 (1:1 ethanol-polyethylene glycol 400 blend), 28 (propylene glycol), 30 (polyethylene glycol 400), 32 (butylene glycol), 34 (hexylene glycol) and 36 (methoxypolyethylene glycol 350).

Each data point identified in the phase diagram of FIG. 5 represents an actual preparation of propylene carbonate, glycerol and a respective one of the aforementioned cosolvents that was produced by the present inventors in connection with research and development of the instant invention. As can be seen in FIG. 5, for each of the cosolvents tested, successful formulations were produced containing glycerol in amounts constituting less than 10 wt % of the composition. At the opposite extreme, single phase preparations were produced containing over 90 wt % glycerol.

Similarly, for all of the solvents represented in FIG. 5, single-phase compositions were produced which contained less than 10 wt % propylene carbonate to as high as about 89 wt % propylene carbonate.

It will be appreciated that the data provided in FIG. 5 merely exemplify a few of the essentially infinite relative quantitative combinations of propylene carbonate, glycerol and cosolvents that may be formulated to produce a single-phase, anhydrous topical preparation consistent with the scope and spirit of the present invention. Hence, suitable single-phase preparations might also be formulated which contain propylene carbonate, glycerol and appropriate cosolvent(s) whose propylene carbonate and glycerol contents may be even greater or less than those depicted in FIG. 5.

Further, any of the anhydrous, single-phase propylene carbonate, glycerol and cosolvent systems graphically depicted in the phase diagram of FIG. 5 constitute compositions formulated according to the present invention that may function, without more, as at least a topical preparation having some measure of skin moisturization efficacy or similar cosmetic/therapeutic characteristics.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A single-phase, clear, anhydrous preparation for topical application, said preparation comprising:

propylene carbonate;

at least one alcohol selected from the group consisting of short chain alcohols and glycols; and at least one ingredient selected from the group consisting of glycerol, a therapeutically active ingredient, and a cosmetically active ingredient, wherein said therapeutically active ingredient or said cosmetically active ingredient is at least one ingredient selected from the group consisting of sunscreening agents, sunblocking agents, anti-inflammatory agents, antioxidants, radical scavenging agents, chelating agents, retinoids, alpha-hydroxy acids, benzofuran derivatives, local analgesics, emollients, antibiotics, antiseptics, antihistamines, N-acetyl-L-cysteine and derivatives thereof, skin protectants, vitamins, and fungicides, wherein said fungicides are selected from the group consisting of imidazoles and azoles.

2. The preparation of claim 1 wherein said therapeutically or cosmetically active ingredient comprises miconazole nitrate.

3. The preparation of claim 1 further comprising a gelling agent.

4. The preparation of claim 1 wherein said preparation includes said glycerol.

5. The preparation of claim 4 wherein said glycerol is present in an amount constituting up to about 45 weight percent of the preparation.

6. The preparation of claim 1 wherein said preparation includes both said glycerol and said therapeutically or cosmetically active ingredient.

7. The preparation of claim 6 wherein said glycerol is present in an amount constituting up to about 45 weight percent of the preparation.

8. The preparation of claim 1 wherein said at least one alcohol selected from the group consisting of short chain alcohols and glycols is selected from the group consisting of ethanol, isopropyl alcohol, butylene glycol, polyethylene glycol, hexylene glycol, methoxypolyethylene glycol, an ethanol-propylene glycol blend and an ethanol-polyethylene glycol blend.

9. The preparation of claim 1 wherein said fungicides are selected from the group consisting of miconazole nitrate, econazole nitrate, itraconazole, saperconazole, oxyconazole, sufaconazole, clotrimazole, terbinafine, amorolfine, fluconazole, ketoconazole, and terconazole.

10. A single-phase, clear, anhydrous preparation for topical application, said preparation comprising:

propylene carbonate;

glycerol; and at least one alcohol selected from the group consisting of short chain alcohols and glycols in an amount sufficient to effectuate miscibility between said propylene carbonate and said glycerol.

11. The preparation of claim 11 wherein said at least one alcohol selected from the group consisting of short chain alcohols and glycols is selected from the group consisting of ethanol, isopropyl alcohol, a 1:1 ethanol-propylene glycol blend, a 1:1 ethanol-polyethylene glycol 400 blend, hexylene glycol, methoxypolyethylene glycol, propylene glycol, polyethylene glycol and butylene glycol.

12. A method of producing a single-phase, clear, anhydrous preparation for topical application comprising combining propylene carbonate, at least one alcohol selected from the group consisting of short chain alcohols and glycols, and at least one ingredient selected from the group consisting of a therapeutically and cosmetically active ingredient in amounts sufficient to produce said single-phase preparation, wherein said therapeutically active ingredient or said cosmetically active ingredient is at least one ingredient selected from the group consisting of sunscreening agents, sunblocking agents, anti-inflammatory agents, antioxidants, radical scavenging agents, chelating agents, retinoids, alpha-hydroxy acids, benzofuran derivatives, local analgesics, emollients, antibiotics, antiseptics, antihistamines, N-acetyl-L-cysteine and derivatives thereof, skin protectants, vitamins, and fungicides, wherein said fungicides are selected from the group consisting of imidazoles and azoles.

13. The method of claim 12 wherein said therapeutically or cosmetically active ingredient comprises miconazole nitrate.

14. The method of claim 12 further comprising adding a gelling agent to said preparation.

15. The method of claim 12 wherein said preparation includes glycerol.

16. The method of claim 15 wherein said glycerol is present in an amount constituting up to about 45 weight percent of the preparation.

17. The method of claim 15 wherein said preparation includes both said glycerol and said therapeutically or cosmetically active ingredient.

18. The method of claim 17 wherein said glycerol is present in an amount constituting up to about 45 weight percent of the preparation.

19. The method of claim 12 wherein said at least one alcohol selected from the group consisting of short chain alcohols and glycols is selected from the group consisting of ethanol, isopropyl alcohol, propylene glycol, butylene glycol, polyethylene glycol, hexylene glycol, methoxypolyethylene glycol, an ethanol-propylene glycol blend and an ethanol-polyethyleneglycol blend.

20. The method of claim 12 wherein said fungicides are selected from the group consisting of miconazole nitrate, econazole nitrate, itraconazole, saperconazole, oxyconazole, sufaconazole, clotrimazole, terbinafine, amorolfine, fluconazole, ketoconazole, and terconazole.

21. A method of producing a single-phase, clear, anhydrous preparation for topical application comprising combining with propylene carbonate and glycerol at least one alcohol selected from the group consisting of short chain alcohols and glycols in an amount sufficient to effectuate miscibility between said propylene carbonate and said glycerol.

22. The method of claim 21 wherein said at least one alcohol selected from the group consisting of short chain alcohols and glycols is selected from the group consisting of ethanol, isopropyl alcohol, a 1:1 ethanol-propylene glycol blend, a 1:1 ethanol-polyethylene glycol 400 blend, hexylene glycol, methoxypolyethylene glycol, propylene glycol, polyethylene glycol and butylene glycol.

23. A method of producing a single-phase, clear, anhydrous preparation for topical application comprising combining:

propylene carbonate;

at least one alcohol selected from the group consisting of short chain alcohols and glycols; and glycerol in amounts sufficient to produce said single-phase preparation.

\* \* \* \* \*